United States Patent [19]
Preti et al.

[11] 4,400,826
[45] Aug. 23, 1983

[54] CRANIOSTATIC POSITIONER, PARTICULARLY FOR THE AMBULATORIAL RADIOGRAPHY OF THE TEMPORAL-MANDIBULAR ARTICULATION

[76] Inventors: Giulio Preti, Strada Costalunga, 10/2 Moncalieri; Franco Mongini, Strada del Nobile, 91 Torino, both of Italy

[21] Appl. No.: 196,946

[22] Filed: Oct. 14, 1980

[30] Foreign Application Priority Data

Oct. 17, 1979 [IT] Italy .............................. 69014 A/79

[51] Int. Cl.³ .......................................... G03B 41/16
[52] U.S. Cl. .................................... 378/178; 378/168; 378/206
[58] Field of Search ........... 250/451, 456, 468, 439 R, 250/439 P, 444, 468, 490, 491

[56] References Cited

U.S. PATENT DOCUMENTS

| | | | |
|---|---|---|---|
| 2,264,410 | 12/1941 | Schier | 250/451 |
| 2,903,588 | 9/1959 | Minnich | 250/451 |
| 3,154,683 | 10/1964 | Blair | 250/451 |
| 3,778,625 | 12/1973 | Schwartz | 250/456 |
| 4,088,893 | 5/1978 | Schroeder | 250/456 |
| 4,144,460 | 3/1979 | Norman | 250/451 |

*Primary Examiner*—Craig E. Church
*Attorney, Agent, or Firm*—Guido Modiano; Albert Josif

[57] ABSTRACT

The craniostatic positioner comprises a pair of plates carried by a transverse yoke and having, one a collimator with a socket for the insertion of the X-ray tube therein, the other a cassette holder with an optical centering device, and a positioning assembly for positioning the patient's head including a headrest, a forehead slider, and an auricolar compass provided with at least one swivelling extension which cooperates with the compass in defining a reference plane containing anatomically definite and selectable points of the skull structure.

7 Claims, 4 Drawing Figures

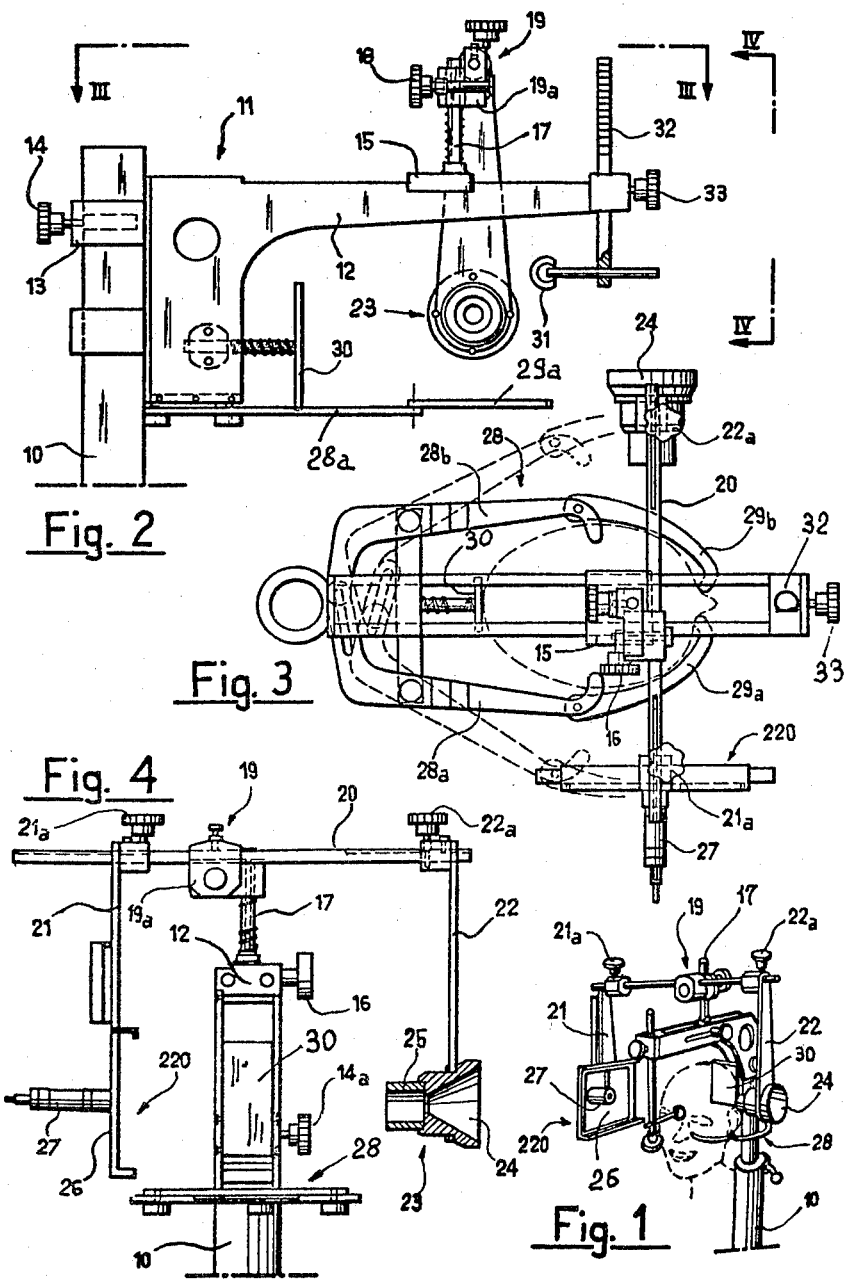

CRANIOSTATIC POSITIONER, PARTICULARLY FOR THE AMBULATORIAL RADIOGRAPHY OF THE TEMPORAL-MANDIBULAR ARTICULATION

BACKGROUND OF THE INVENTION

This invention relates to an improved craniostatic positioner hereinafter called "craniostat," particularly for the ambulatorial radiography of the temporal-mandibular articulation.

The radiographic survey of the temporal-mandibular articulation requires—as is well known to the expert in the art—a highly accurate positioning of the X-ray tube, in order to prevent interferences and the formation of images wherein different elements of the cranial structure and/or the vertebral column overlap one another. This positioning is effected by suitably tilting the collimator of the X-ray tube relatively to the patient's skull which is generally held in an erect posture.

For this purpose, conventional craniostats make use of a semicircular stand, at one end whereof there is arranged the collimator, and at the other end the cassette holder intended for receiving the radiograph sensitive plate. The half circle, which is suspended from a central pivot pin, is enabled to rotate about a perpendicular axis to its equatorial plane, and to tilt to various inclination angles by rotation in the meridian plane which contains it.

That known structure has several drawbacks, and in particular the disadvantage arising from the lack of a reference plane defined on the patient's skull, whereto the rotation and tilt angles of said craniostat stand can be related. In fact, lacking that reference, the examination repeatability, especially after some time, becomes unattainable or at least questionable owing to the patient's head being unlikely to exactly occupy each time the same position relatively to the craniostat.

SUMMARY OF THE INVENTION

This invention sets out, in essence, to eliminate the latter drawback such as to enable, on one side, the attainment of correct images, and on the other side, the repeatability of the examinations and consequent clinic comparability of radiographs even when taken at long time intervals, with evident advantages for the physician who is to provide an interpretation of the radiographs.

A further important object of the invention is to provide a craniostat which is structurally simple, easy to use, and above all associable with the radiologic equipment most commonly employed in odontoiatric ambulatories.

According to one aspect of the present invention, there is provided an improved craniostat, particularly for the ambulatorial radiography of the temporal-mandibular articulation, characterized in that it comprises a cantilevered stand or support carried for controlled height adjustment at the end of a columnar upright rigid with a seat, a supporting pivot pin carried by a slider arranged to be slidable on the horizontal arm of said cantilevered stand and subjected to controlled displacement parallel to said arm, a transverse yoke carried by said pivot pin for angular oscillation in the vertical plane containing said yoke, a pair of plates carried at the ends of said yoke and enabled to controllably move parallel to the axis of said yoke and rotate about said axis, one of said plates carrying at the free end thereof a collimator with a socket for the insertion of the X-ray tube therein, the other of said plates carrying at the free end thereof a cassette holder provided with a luminous centering device set coaxially to said collimator, and a means for positioning the patient's head relatively to the craniostat including a headrest and a forehead slider, both said headrest and said forehead slider being adjustable, as well as an auricolar compass provided with at least one swivelling extension adapted for cooperating with the patient's auricolar cavities in defining a reference plane containing anatomically definite and selectable points of the patient's cranial structure.

BRIEF DESCRIPTION OF THE DRAWING

Further features and advantages will be more clearly apparent from the detailed description which follows, with reference to the accompanying drawings, given herein by way of example only, and where:

FIG. 1 is a perspective view of the improved craniostat according to this invention;

FIG. 2 is a side elevation view thereof;

DESCRIPTION OF THE PREFERRED EMBODIMENTS

Figure 6:
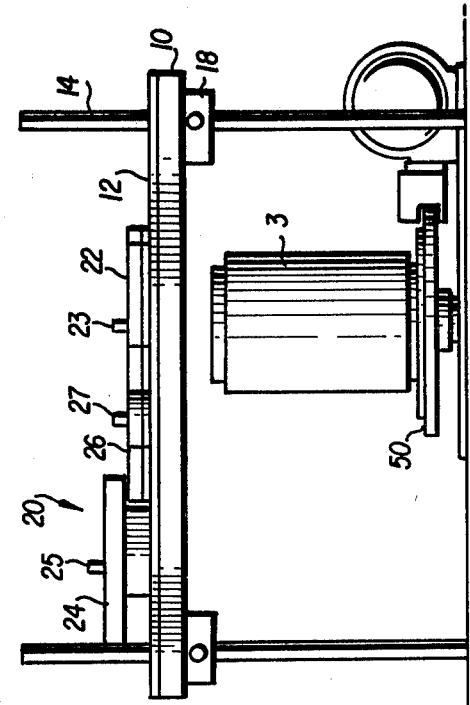
Figure 5:
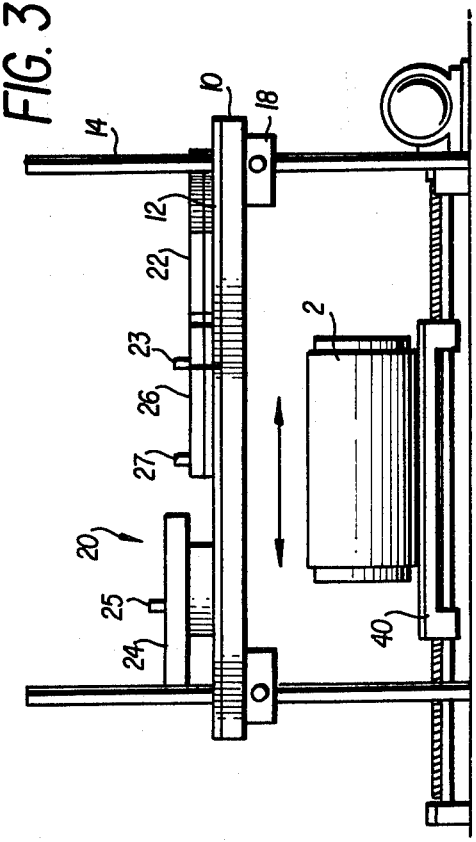
Figure 4:
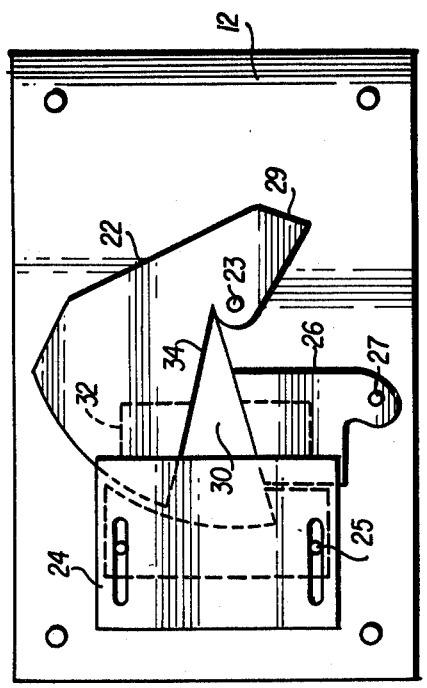
FIG. 4 is a front elevation view in the direction of the arrows IV—IV of FIG. 2.
Figure 3:
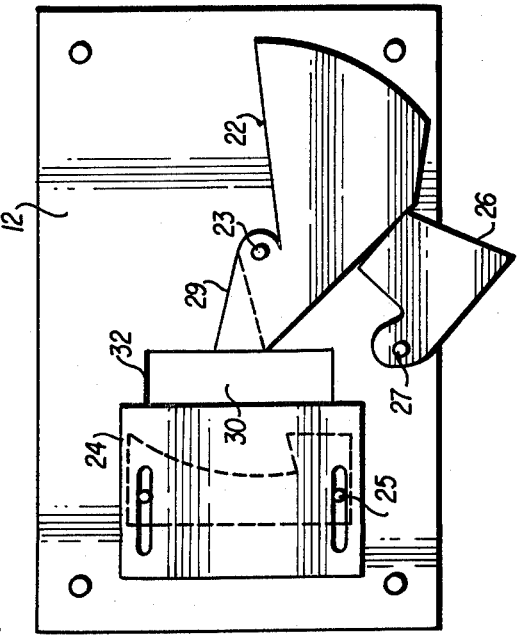
FIG. 3 is a top plan view in the direction of the arrows III—III of FIG. 2.

In the drawing figures, the reference numeral 10 designates a cylindrical upright of columnar configuration which is made rigid with a seat (not shown) of the type mounted on caster wheels. The top end of the upright carries, with provision for height adjustment, a stand or bracket 11 provided with a horizontal arm 12. Advantageously, the stand or bracket has ring supports 13 which can slide along the upright 10 and be locked at the selected adjustment position by means of a setscrew 14; the height adjustment being effected by means of a rack and pinion type of mechanism which can be actuated through a knob 14a. On the horizontal arm 12, there is arranged a seat with retaining guides or runways for a slider 15 which can be moved axially along said arm, it being controlled to perform such movements by means of a rack and pinion mechanism which can be operated through a knob 16 protruding sideways from said arm. The slider 14 carries a pivot pin 17, having a vertically extending axis, whereon there is mounted—with provision for vertical adjustment through a rack and pinion mechanism controlled by a further knob 18—a horizontally extending swivel joint 19.

The movable part 19a of said swivel joint carries a yoke comprising a transverse rod 20 which is enabled, accordingly, to complete angular oscillations in the vertical plane which contains it. On the rod of said yoke, there are supported for sliding movement—with provision for adjustment in the axial direction through rack and pinion mechanisms operated by means of respective knobs, 21a-22a—two ear plates 21-22 which extend downwards and carry, the former a cassette holder 220 intended for containing the radiograph sensitive plate, and the latter a collimator 23 having a conically tapered socket 24 for the insertion therein of the radiogenic tube (not shown) which is a part of the radiologic apparatus.

The insertion of the X-ray tube into the conical socket 24 is carried out by first applying on the end of the tube a synthetic resin forming at the tube end a conical insertion plug matching said socket. Moreover, a lead tube 25 is associated with the collimator 23 which serves for gathering the central portion of the X-ray beam where the rays are parallel to one another and perpendicular to the structure being X-rayed.

The cassette holder 220 is provided with a clear or transparent wall 26 whereto an optical centering device 27 is secured which comprises a light source and an optical lens system forming a luminous pencil which extends perfectly coaxial to the collimator 24.

At the lower or bottom end of the stand or bracket 11, there is arranged an auricolar compass 28 including two spreadable apart arms 28a–28b with bent terminations intended to fit in the auricular cavities of the patient. Furthermore, to the ends of said arms, there are articulated two small bars 29a–29b enabling—as will be explained hereinafter—the reference plane to be selected.

This craniostat further comprises a means of positioning the patient's head, which comprises a headrest 30 and a forehead slider 31 carried at the lower or bottom end of a rod 32 capable of being adjusted vertically by means of a rack and pinion mechanism through a knob 33.

The craniostat according to this invention is utilized in the following manner.

The patient, from a sitting position, introduces his/her head between the plates 21–22, which to facilitate the operation, are purposely made tiltable in common upwardly by rotation about the axis of the rod 20; the arms of the auricolar compass 28 being at this stage in their spread apart position.

Then the ends of the arms of the auricolar compass 28a–28b are inserted in the auricolar cavities of the external ear and the patient's head is turned to select the reference plane containing said arms and the bars 29a–29b. Assuming that the Camper plane is selected for the reference plane, the ends of the bars will be moved—by turning the patient's head about an ideal axis led through the ends of the auricolar compass arms—to a position at the patient's nose wing. Naturally, with a different rotation of the patient's head, it would become possible to select any other reference plane, e.g. the Frankfurt plane which contains said auricolar axis and the lower edge of the orbit.

After the patient's head has been positioned in conformity with the selected reference plane, the headrest 30 is brought into contact and the forehead slider 31 is pushed into the glabella, it having been pre-adjusted in height by means of the knob 33. The level whereat the slider has been positioned can be read on graduations provided on the rod 32, and represents an item of information to be recorded on the patient card for repeatability of the examination.

At this stage, by tilting the yoke 20 in the vertical plane, the luminous spot of the centering device 27, which is visible through the wall 26, is brought into alignment with a mark previously applied with a dermographic pencil on the patient's head at the articulation to be X-rayed. The inclination angle is measured by means of a goniometer etched on the movable part 19a of the joint 19, and represents a further item of information to be recorded for future repeatability. Subsequently, the knob 21a is operated to bring the cassette holder 220 as close as possible to the patient's head, and accordingly to the structure to be X-rayed, for the purpose of obtaining images which more closely approximate the actual dimensions, and the radiograph is taken.

It should be noted that the provision of the gathering tube 25, in addition to improving the quality of the radiograph—by virtue of the absence of scattered rays—affords the possibility of taking two radiographs on each plate, with obvious attendant advantages of an economical nature and greater analysis convenience.

Obviously, within the principle of this inventive concept, the actual details and shapes may vary rather amply from what has been described and illustrated herein by way of example and not of limitation, without departing from the invention scope.

We claim:

1. A craniostat, particularly for the ambulatorial radiography of the temporal-mandibular articulation, characterized in that it comprises a cantilevered stand or support carried for controlled height adjustment at the end of a columnar upright rigid with a seat, a supporting pivot pin carried by a slider arranged to be slidable on the horizontal arm of said cantilevered stand and subjected to controlled displacement parallel to said arm, a transverse yoke carried by said pivot pin for angular oscillation in the vertical plane containing said yoke, a pair of plates carried at the ends of said yoke and enabled to controllably move parallel to the axis of said yoke and rotate about said axis, one of said plates carrying at the free end thereof a collimator with a socket for the insertion of the X-ray tube therein, the other of said plates carrying at the free end thereof a cassette holder provided with a luminous centering device set coaxially to said collimator, and a means for positioning the patient's head relatively to the craniostat including a headrest and a forehead slider, both said headrest and said forehead slider being adjustable, as well as an auricolar compass provided with at least one swivelling extension adapted for cooperating with the patient's auricolar cavities in defining a reference plane containing anatomically definite and selectable points of the patient's cranial structure.

2. A craniostat according to claim 1, wherein the controlled displacement of said stand, slider, plates, and forehead slider is effected through rack and pinion mechanisms actuatable by means of respective control knobs.

3. A craniostat according to claim 1, wherein the connecting member of said yoke to said vertical pivot pin carried by said slider comprises a horizontal axis swivel joint having a stationary part and a movable part, respectively connected to said pivot pin and to the rod of said yoke, and wherein said movable part has a goniometric scale etched thereon and said stationary part a fixed reference, or viceversa, for the purpose of measuring and recording the inclination angle imparted to said yoke for each patient.

4. A craniostat according to claim 1, wherein said forehead slider is carried at the end of a rod having a graduated scale thereon for the purpose of measuring and recording the positioning level thereof for each patient.

5. A craniostat according to claim 1, wherein said socket for the insertion of the X-ray tube into the collimator is conically tapered to receive a matching extension at the end of said X-ray tube pre-molded from a synthetic resin.

6. A craniostat according to claim 1, wherein said collimator is provided with a radiation gathering tube adapted for selecting, for the formation of the radiograph, solely those rays which are perpendicular to the structure being X-rayed.

7. A craniostat according to claim 6, wherein said optical centering device comprises a light source cooperating with a focussing lens system and is supported by a transparent wall of said cassette holder.

* * * * *